United States Patent [19]

Young et al.

[11] Patent Number: 4,906,771

[45] Date of Patent: Mar. 6, 1990

[54] PROCESS FOR CATALYTIC OXIDATION OF ORTHO-NITROAROMATIC COMPOUNDS TO ORTHO-NITROAROMATIC ACIDS

[75] Inventors: David A. Young, Warrenville; Mary E. Volling, Joliet, both of Ill.

[73] Assignee: Amoco Corporation, Chicago, Ill.

[21] Appl. No.: 301,814

[22] Filed: Jan. 25, 1989

Related U.S. Application Data

[63] Continuation-in-part of Ser. No. 112,484, Oct. 26, 1987, abandoned.

[51] Int. Cl.$^4$ ............................................. C07C 51/265
[52] U.S. Cl. ...................................... 562/416; 562/413
[58] Field of Search ................................ 562/416, 413

[56] References Cited

U.S. PATENT DOCUMENTS

| | | | |
|---|---|---|---|
| 3,030,414 | 4/1962 | Barker | 562/416 |
| 3,030,415 | 4/1962 | Fields | 562/416 |
| 4,007,223 | 2/1977 | Feld | 562/416 |

FOREIGN PATENT DOCUMENTS

| | | | |
|---|---|---|---|
| 58-183645 | 10/1983 | Japan | 562/416 |
| 58-183646 | 10/1983 | Japan | 562/416 |
| 811870 | 4/1959 | United Kingdom | 562/412 |

Primary Examiner—Michael L. Shippen
Attorney, Agent, or Firm—Gunar Blumberg; William H. Magidson; Ralph C. Medhurst

[57] ABSTRACT

A process for producing ortho-nitroaromatic acids in high yields is disclosed. The process comprises reacting an ortho-nitroaromatic having at least one nitro group ortho to at least one oxidizable group with molecular oxygen in an inert reaction medium in the conjoint presence of a co-oxidizable compound, a heavy metal catalyst and bromine.

58 Claims, No Drawings

PROCESS FOR CATALYTIC OXIDATION OF ORTHO-NITROAROMATIC COMPOUNDS TO ORTHO-NITROAROMATIC ACIDS

This is a continuation-in-part of patent application Ser. No. 112,484, filed Oct. 26, 1987, abandoned.

FIELD OF THE INVENTION

The field of this invention relates to a process for the catalytic oxidation of an ortho-nitroaromatic to an ortho-nitroaromatic acid wherein the ortho-nitroaromatic has an oxidizable group located next to the nitro group on the aromatic ring and preferably where the oxidizable group is a methyl group. More particularly, this invention relates to the autoxidation of an ortho-nitroaromatic in the presence of a co-oxidizable compound by means of air or other molecular oxygen-containing gaseous material to an ortho-nitroaromatic acid wherein the oxidation catalyst comprises manganese and bromine components, or cobalt and bromine components, or cobalt, manganese and bromine components, or alternately, cobalt, manganese, zirconium and bromine components.

BACKGROUND OF THE INVENTION o-Nitroaromatic acids are used in a variety of applications. For example, o-nitrobenzoic acid is a high value, low volume, specialty chemical which is used primarily as a corrosion inhibitor. However, anthranilic acid (2-aminobenzoic acid) can be prepared by hydrogenation of o-nitrobenzoic acid. Anthranilic acid has applications in dyes, pharmaceuticals, perfumes, pigments, flavors, and as an antioxidant in greases and lubricating oils. An economic low-cost method of preparing o-nitrobenzoic acid accordingly is of economic value to prepare anthranilic acid.

The most common route to form anthranilic acid consists of a Hoffman degradation of phthalamic acid alkali metal salt, or phthalimide. Anthranilic acid is also produced by the reduction of o-nitrobenzoic acid, which is formed from the oxidation of o-nitrotoluene with permanganate, or with chromic acid and sulfuric acid. An alternative method for the formation of anthranilic acid is the treatment of isatin with hot 40% potassium hydroxide.

2-Nitroterephthalic acid is also a useful o-nitroaromatic acid. Applications include its use as a corrosion inhibitor, heat transfer agent, polymerization inhibitor and as a catalyst for curing inks and coatings. 2-Nitroterephthalic acid is also a useful chemical intermediate. For example, the nitro group may be hydrogenated to an amino group to prepare 2-amino-terephthalic acid. Alternatively, the nitro group may be readily displaced by active nucleophilic agents such as methoxide or phenoxide. The nucleophilic displacement of the nitro group with, for example, a methoxy group would produce 2-methoxyterephthalic acid whereas the displacement with a phenoxy group would produce 2-phenoxy-terephthalic acid. These and other 2-substituted terephthalic acid compounds that can be prepared from 2-nitroterephthalic acid are useful monomers for the formulation of heat processible polymeric materials. Furthermore, we have determined that 2-nitroterephthalic acid is not readily prepared by the nitration of terephthalic acid.

It has been known that while meta and para-nitrotoluene are readily oxidized by means of molecular oxygen in the presence of bromine and a heavy metal oxidation catalyst to the corresponding nitrobenzoic acid, the corresponding ortho isomer, namely ortho-nitrotoluene, is unexpectedly resistant to oxidation by this process. Similarly, other ortho-nitrosubstituted aromatics, such as 2-nitro-paraxylene are unexpectedly resistant to oxidation. It is particularly surprising that ortho-nitrotoluene does not oxidize in this process, since there is no difficulty observed in the chemical oxidation of ortho-nitrotoluene. For example, potassium dichromate and sulfuric acid have been employed to give high yields of ortho-nitrobenzoic acid (see Org. Chem. Ind. (U.S.S.R.), 7, p. 379 (1940)) and similar results have been obtained with boiling aqueous permanganate, e.g. as reported by M. Boetius, Berichte Deutsche Chemische Gesellschaft (Ber., 68B, p. 1924 (1935)). It has also been reported that when boiled with a sodium hydroxide solution, orthonitrotoluene exhibits the phenomena of autoxidation and reduction and yields anthranilic acid (Kirk-Othmer, *Encyl. Chem. Tech.*, 15, 3rd, p. 926).

General background references using the Hoffmann degradation of phthalamide derivatives to prepare anthranilic acid or the oxidation of ortho-nitrotoluene with expensive permanganate and chromic acid are disclosed in the following patents: Romanian Patent No. 74,453, Romanian Patent No. 79,909, U.S. Pat. No. 4,233,459, U.S. Pat. No. 4,276,433, U.S. Pat. No. 3,847,974, U.S. Pat. No. 3,322,820, U.S. Pat. No. 3,882,171, French Patent No. 2,512,844, and Japanese Patent No. 57,026,652.

Various attempts have been made in the past to oxidize ortho-nitrotoluene by autoxidation wherein the reaction is catalyzed by transition metal and bromide ions in acetic acid. As reported by R. Hasegawa and Y. Kamiya, *Bul. Chem. Soc.* Japan, 51, No. 5, 1490–94 (1978), proceeding only to ortho-nitroacetophenone, ortho-nitroalkylbenzenes, except ortho-nitroethylbenzene, shows a great resistivity against the oxidation, with the authors describing the results as explained by the retardation effect due to inactive free radicals and also to the various reduced products resulting from the intra-molecular reaction of various nitro groups and active radicals.

An object of this invention accordingly is to provide a process for the oxidation of an ortho-nitroaromatic to an ortho-nitroaromatic acid in high yield. These orthonitroaromatics have a group positioned next to the nitro group on the aromatic ring wherein the group is oxidizable to a carboxylic acid. Another object of this invention is to prepare ortho-nitroaromatic acids by the oxidation of an ortho-nitroaromatic by means of molecular oxygen in the presence of bromine and a heavy metal oxidation catalyst. It is further an object of this invention to prepare ortho-nitroaromatic acids from an ortho-nitroaromatic compound by autoxidation in the presence of bromine and a heavy metal oxidation catalyst and a co-oxidizable compound.

A further object is to provide an oxidation process employing a solvent medium from which ortho-nitrobenzoic acid can be obtained directly and in high yield and high purity. These and other objects of this invention will be apparent from the ensuing description thereof.

DETAILS OF THE INVENTION

In accordance with the process of this invention, an ortho-nitroaromatic is reacted with molecular oxygen in the liquid phase in the presence of a lower saturated aliphatic monocarboxylic acid solvent, and a co-oxidizable compound, and in the presence of a catalyst comprising in conjoint presence bromine and a heavy metal oxidation catalyst.

The ortho-nitroaromatics that are oxidized to the corresponding ortho-nitroaromatic acid by the process of this invention are those nitro-aromatic compounds that have a nitro group positioned on the aromatic ring ortho to an oxidizable group. While the oxidizable group is typically a methyl, ethyl or propyl group, any group that can be oxidized to a carboxylic acid functionality is suitable. A methyl group is the preferred oxidizable group and ortho-nitroaromatic compounds having nitro groups ortho to methyl groups are the preferred ortho-nitroaromatics oxidizable by the processes of this invention.

In addition to the oxidizable group ortho to the nitro group, the aromatic compound may be substituted with other oxidizable groups so that oxidation of the aromatic compound will provide di-, tri-, tetra- or polycarboxylic nitroaromatic acids.

The aromatic portion of the ortho-nitroaromatic compounds that can be oxidized by the process of this invention may be a single aromatic ring such as a benzene nucleus, or it may contain multiple aromatic rings such as biphenyl, terphenyl, naphthalene, anthracene, etc. In addition, the aromatic ring or rings may be comprised entirely of carbon atoms or may, in addition, contain heteroaromatic atoms such as, for example, nitrogen. Furthermore, the aromatics may be substituted with a variety of substituents that are either completely inert to the oxidation conditions, such as the halogens, or that can be transformed under the oxidation conditions of this invention, for example, the oxidation of a phenyl methane moiety to a phenyl ketone moiety.

Furthermore, the ortho-nitroaromatic compounds oxidizable by this invention may have more than one nitro group per aromatic nucleus and there may be more than one oxidizable group ortho to each nitro group.

Ortho-nitrotoluene and 2-nitro-paraxylene are the preferred ortho-nitroaromatic compounds for the process of this invention, and they are oxidized to form o-nitrobenzoic acid and 2-nitroterephthalic acid, respectively.

Ortho-nitrotoluene can be obtained by separation of ortho-nitrotoluene from isomeric mixtures of nitrotoluenes, which are readily obtained by the mono-nitration of toluene in accordance with methods well-known in the art. Such mixtures generally contain 30–70% by weight of para-nitrotoluene, 70–30% by weight ortho-nitrotoluene and from 0 to about 10% by weight of meta-nitrotoluene. Typically mono-nitration of toluene results in a product consisting of about 55–60% of ortho-, about 40% of para- and about 3% of meta-nitrotoluene. Mixtures of nitrotoluenes containing lower concentrations of para-nitrotoluene within the indicated range can be obtained by controlled nitration of toluene under specific conditions known to the art and by fractional distillation of the usual nitration mixture, a part of the ortho-nitrotoluene being distilled overhead.

2-Nitro-paraxylene may be prepared by a variety of methods, however, the most straightforward method is the nitration of p-xylene using standard aromatic nitration conditions according to methods well-known in the art.

It is essential for the instant novel process that the reaction zone contain a co-oxidizable compound, defined as an alkyl aromatic compound capable of undergoing oxidation in the reaction zone, and the reactant, an ortho-nitroaromatic with an oxidizable group next to the nitro group, in the presence of a catalyst comprising in conjoint presence bromine and a heavy metal oxidation catalyst.

When the o-nitroaromatic acid product is soluble in the reaction medium, a preferred aromatic co-oxidizable compound is a compound that is readily oxidized to an aromatic acid that is extremely insoluble in the reaction solvent medium. This allows for a simple separation between the oxidation product of the co-oxidizable compound and the o-nitroaromatic acid. Preferably, the co-oxidizable compound also produces a valuable oxidation product.

In the event that the product obtained from oxidizing the ortho-nitroaromatic compound is insoluble in the solvent medium used for the oxidation, the material selected as the co-oxidizable compound should be one where its oxidation product is soluble in the reaction medium. In this way effective separation will also be achieved.

In the novel process polyalkylaromatic compounds are suitable as co-oxidizable compounds, the preferred co-oxidizable compounds are toluene and para-xylene. Other suitable co-oxidizable compounds include para-nitrotoluene, meta-xylene, meta-nitrotoluene, para-chlorotoluene, paramethoxytoluene and 4,4'-dimethyldiphenylether. Mixtures of co-oxidizable compounds may also be useful.

Preferably, the oxidation is conducted under liquid-phase conditions in the presence of an oxidation resistant reaction medium in which the organic reactants are soluble or suspended. Inert reaction media which can be employed are materials which are substantially inert to oxidation and which facilitate carrying out the reaction and recovering the desired ortho-nitroaromatic acid. Desirably, the added medium is a lower saturated aliphatic monocarboxylic acid containing from about 2 to about 8 carbon atoms in the molecule, preferably from about 2 to about 4 carbon atoms, and especially acetic acid. Benzoic acid is also a preferred solvent. Mixtures of such acids may be used. When all the advantages of an acid medium are not required, other inert media may be used, such as benzene, carbon tetrachloride, chlorinated hydrocarbons such as chlorinated benzenes or chlorinated naphthalenes and the like, or mixtures thereof with acetic acid or other lower aliphatic monocarboxylic acids.

Where the lower aliphatic monocarboxylic acid medium is used, it is generally not necessary to use large amounts thereof. Such acids in the range of about 0.1 to about 10 parts by weight, desirably about 0.5 to about 4 and preferably about 1 to about 2.5 per part of aromatic material have been found adequate. The amount of solvent employed is selected with a view to facilitating the oxidation reaction and recovery of the oxidation products. For example, in the oxidation of mixtures of isomeric nitrotoluenes to produce ortho-nitrobenzoic acid, the lower carboxylic acids such as acetic acid, propionic acid, n-butyric acid, isobutyric acid, n-valeric acid, trimethylacetic acid and caproic acid, and water, and mixtures thereof, offer particular advantages as solvents since pure ortho-nitrobenzoic acid may be readily separated from the reaction mixture. Acetic acid and water may be readily distilled from ortho-nitrobenzoic acid.

Preferably, the solvent is a mixture of acetic acid and water, which more preferably contains from about 1 to about 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude ortho-nitroaromatic acid product, at least a portion of the mother liquor (solvent) in the resulting product stream is generally recycled to the reactor.

The source of molecular oxygen employed in the oxidation step of the method for producing the ortho-nitroaromatic acid for use in combination with the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from about 0.5 to about 8 volume percent oxygen (measured on a solvent-free basis). For example, in the oxidation of an ortho-nitroaromatic where the oxidizable groups are methyl groups, a feed rate of the oxygen-containing gas sufficient to provide oxygen in the amount of from about 1.5 to about 2.8 moles per methyl group will provide such 0.5 to 8 volume percent of oxygen (measured on a solvent-free basis) in the gas-vapor mixture in the condenser.

Catalysts which have heretofore been employed for accelerating the oxidation of organic compounds, such as the polyvalent metals having atomic weights between about 50 to 59 are advantageously employed as heavy metal oxidation catalysts. Of the heavy metal group, those metals having an atomic number from about 23 to about 28 including vanadium, chromium, manganese, iron, cobalt and nickel are particularly useful as catalysts. These catalysts are suitably employed singly or as mixtures. Particularly good results are obtained with a metal of the group comprising manganese, cobalt and mixtures thereof.

The catalyst employed in the oxidation step of the instant invention for use in combination with the method of this invention comprises manganese and bromine components, or cobalt and bromine components, or cobalt, manganese, and bromine components, or cobalt, manganese, zirconium and bromine components. Suitably, accelerators known in the art are also employed from time to time.

Illustratively, the catalyst is advantageously a heavy metal bromide, for example, manganese bromide, or cobalt bromide, and is suitably added as such or by means of materials which provide a catalytic amount of heavy metal and of bromine to the reaction system. The amount of catalyst, for example of manganese and bromine, calculated as $MnBr_2$ is suitably in the range of about 0.1 to about 10 percent by weight of the aromatic reactant charged, desirably about 0.3 to about 2 and preferably about 0.5 to about 1.5 percent. Mixtures of materials are suitably used, and the proportions of heavy metal oxidation catalyst and bromine is suitably varied from their stoichiometric properties encountered in heavy metal bromides such as $MnBr_2$, for example in the range of about 1 to about 10 atoms of heavy metal per atom of bromine to about 1 to about 10 atoms of bromine per atom of heavy metal. Similarly, an amount of catalyst, as for example, cobalt and bromine, calculated as $CoBr_2$, is suitably in the range of about 0.1 to about 10 percent by weight of the aromatic reactant charged, advantageously about 0.3 to about 2, and preferably about 0.5 to about 1.5 percent.

The weight ratio of cobalt (calculated as elemental cobalt) metal in the liquid-phase oxidation is in the range of from about 0.2 to about 10 milligram atoms (mga) per gram mole of polyalkyl aromatic. The weight ratio of manganese (calculated as elemental manganese) in the manganese component of the catalyst in the liquid-phase oxidation is in the range of from about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.2 to about 1.5 mga per mga of total cobalt and manganese.

The metal catalyst is suitably added in elemental, combined or ionic form, for example as the free metal, as the oxide or hydroxide, or in the form of metal salts. For example, the metal manganese is suitably supplied as the manganese salt of a lower aliphatic carboxylic acid, such as the acetate, as the salt of a fatty acid or other organic acid, such as manganese naphthenate, or in the form of an organic complex such as the acetylacetonate, $\beta$-hydroxy-quinolinate, or the like, as well as inorganic manganese salts such as the borates, halides, nitrates, etc. Both of the cobalt and manganese components are suitably provided in any of their known ionic or combined forms that provide soluble forms of cobalt, manganese, and bromine in the solvent in the reactor. When the solvent is an acetic acid medium, cobalt and/or manganese carbonate, acetate tetrahydrate, and/or bromide is suitably employed.

Similarly, the bromine is suitably added in elemental, combined or ionic form. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of about 0.2:1.0 to about 1.5:1.0. The bromine ion released from the organic bromides at the oxidation operating conditions are readily determined by known analytical means. Tetrabromoethane, for example, at operating temperatures of about 170° C. to about 225° C. has been found to yield about 3 effective gram atoms of bromine per gram mole. The bromine compounds are suitably insoluble or partially soluble in the reaction medium.

In operation, the minimum pressure at which the oxidation reactor is maintained is that pressure which will maintain a substantial liquid phase of the ortho-nitroaromatic and at least 70% of the solvent. The ortho-nitroaromatic and solvent not in the liquid phase because of vaporization are suitably removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm$^2$ to about 35 kg/cm$^2$, and typically are in the range of from about 10 kg/cm$^2$ to about 30 kg/cm$^2$. The temperature range to oxidize the ortho-nitroaromatic within the oxidation reactor is generally from about 250° F., to about 400° F. The reaction is suitably carried out at a pressure of about 150 psig to about 400 psig, suitably from about 200 psig to about 300 psig. The solvent residence time in the oxidation reactor is generally from about 20 to about 200 minutes and preferably from about 30 to about 140 minutes. After the ortho-nitroaromatic is oxidized to an ortho-nitroaromatic acid, the temperature is elevated from the nitroaromatic oxidation temperature to about 380° F. to about 430° F. to oxidize all the co-oxidizable compound, thus assuring ease of product separation. The co-oxidizable compound may be added semi-continuously and in some cases this is the preferred method of addition.

In a preferred embodiment, ortho-nitrotoluene is oxidized by air using a catalyst containing cobalt (II) acetate, manganese (II) acetate, and hydrogen bromide in the presence of a co-oxidizable compound comprising para-xylene or para-nitrotoluene. The catalyst package optionally includes zirconium acetate and any ionic bromine source. The co-oxidizable compounds are suitably para-xylene, meta-xylene, para-nitrotoluene, meta-nitrotoluene, para-chlorotoluene, para-methoxytoluene, and 4,4'-dimethyldiphenylether. The oxidation temperature to oxidize the ortho-nitrotoluene is critical and should be in the range of from about 250° F. to about 360° F., preferably about 295° F. to about 350° F. Oxidation temperatures greater than about 380° F, such as 390° F. to about 420° F., result in no detectable o-nitrobenzoic acid in the oxidation product. The temperatures used to complete the oxidation of the co-oxidizable compound are about 380° F. to about 410° F. The oxidation of the co-oxidizable material facilitates the ease of separation of the product, orthonitrobenzoic acid.

Purification of the ortho-nitrobenzoic acid is obtained by cooling the total reactor effluent to about 220° F. to about 260° F. by a quick flash and filtration of the p-nitrobenzoic acid or terephthalic acid. The mother liquor is stripped leaving o-nitrobenzoic acid and the catalyst components. This residue is extracted with water, cooled to about 35° F. to about 60° F., and filtered to give pure o-nitrobenzoic acid. The o-nitrobenzoic acid can be hydrogenated in an appropriate reaction to give anthranilic acid.

In another preferred embodiment, 2-nitro-paraxylene is oxidized by air using a catalyst containing cobalt (II) acetate, manganese II acetate, hydrogen bromide in the presence of a co-oxidizable compound comprising toluene. The catalyst package optionally includes zirconium. The zirconium may be in the form of zirconium acetate. The oxidation temperature to oxidize the 2-nitro-para-xylene is in the range of from about 250° F. to about 400° F. The temperature used to complete the oxidation of the co-oxidizable compound is in the range of from about 380° F. to about 430° F. The oxidation of the co-oxidizable compound facilitates the ease of separation of the product, 2-nitroterephthalic acid.

In summary, the novel process comprises a process for producing ortho-nitroaromatic acids by oxidizing an ortho-nitroaromatic having at least one nitro group ortho to at least one oxidizable group which comprises oxidizing the ortho-nitroaromatic with molecular oxygen in a reaction zone at a temperature within the range of from about 250° F. to about 400° F. and a pressure from about 150 psig to about 400 psig in the presence of an inert reaction medium, while maintaining a liquid phase in said zone, and wherein the reaction is conducted in the conjoint presence of a co-oxidizable compound and a heavy metal catalyst and bromine, and recovering the ortho-nitroaromatic acid. The heavy metal advantageously has an atomic number of about 23 to about 28 inclusive, the bromine is in ionic form, and the co-oxidizable compound is an alkyl aromatic compound. Advantageously, the alkyl aromatic compound includes one or more of the following: para-xylene, para-nitrotoluene, meta-xylene and toluene. Preferably, the aromatic compound capable of undergoing co-oxidation is para-xylene or toluene. The heavy metal is suitably manganese, or cobalt, or manganese and cobalt, or manganese, cobalt and zirconium. The preferred orthonitroaromatics oxidized by the process of this invention are those ortho-nitroaromatics that have nitro groups ortho to methyl groups.

In the novel process, the co-oxidizable compound is suitably oxidized at a temperature of about 250° F. to about 430° F., advantageously the co-oxidizable compound is oxidized at a temperature of about 295° F. to about 430° F., preferably from about 380° F. to about 430° F. The ortho-nitroaromatic acid is suitably recovered by cooling the total reactor effluent to a temperature of about 220° F. to about 260° F., removing the co-oxidized product acid by filtration, stripping the mother liquor, and extracting with water at a temperature of about 180° F. to about 212° F., cooling the reactor effluent to about 35° F. to about 60° F. and filtering to give the ortho-nitroaromatic acid. Suitably, the co-oxidizable compound is added semi-continuously during the oxidation and the co-oxidizable compound is para-xylene or toluene, in the presence of a monocarboxylic acid having about 1 to about 8 carbon atoms in the molecule. Advantageously, the monocarboxylic acid is acetic acid. Preferably, the novel process comprises a process for producing ortho-nitrobenzoic acid which comprises reacting ortho-nitrotoluene with molecular oxygen in a reaction zone, containing an aliphatic monocarboxylic acid containing about 2 to about 4 carbon atoms, while maintaining a liquid phase in said zone, wherein paraxylene, the co-oxidizable compound, is added throughout the reaction and wherein the reaction is carried out in the presence of cobalt and manganese and bromine and wherein the ortho-nitrobenzoic acid is recovered. In the novel process, the monocarboxylic acid is acetic acid and the oxidation is carried out at a temperature of about 250° F. to about 360° F., preferably the oxidation is carried out at a temperature of about 295° F. to about 350° F., and the co-oxidizable compound is oxidized at a temperature of about 295° F. to about 410° F. The ortho-nitrobenzoic acid is recovered by cooling the total reactor effluent to a temperature of about 220° F. to about 260° F., by stripping the mother liquor, and extracting the mother liquor with water at a temperature of about 180° F. to about 212° F. and cooling the reactor effluent to about 35° F. to about 60° F. and filtering the reactor effluent to give ortho-nitrobenzoic acid.

Preferably, the novel process also comprises a process for producing 2-nitroterephthalic acid which comprises reacting 2-nitro-para-xylene with molecular oxygen in a reaction zone, containing an aliphatic monocarboxylic acid containing about 2 to about 4 carbon atoms, while maintaining a liquid phase in said zone, wherein toluene, the co-oxidizable compound, is added throughout the reaction and wherein the reaction is carried out in the presence of cobalt and manganese and bromine and wherein the 2-nitroterephthalic acid is recovered. In the novel process, the monocarboxylic acid is acetic acid and the oxidation is carried out at a temperature of about 295° F. to about 400° F., and the co-oxidizable compound is oxidized at a temperature of about 295° F. to about 430° F., and preferably at a temperature of from about 350° F. to about 420° F.

The following examples further illustrate the preferred embodiments of this invention. It will be understood that the examples are for illustrative purposes only and do not purport to be wholly definitive with respect to the conditions and scope of the invention.

EXAMPLE I

Ortho-nitrotoluene (19.817 g), cobalt (II) acetate (0.257 g), manganese (II) acetate (0.256 g), sodium bromide (0.210 g) and acetic acid (200.5 g) were introduced into a glass minireactor. Cobalt (III) triacetate (2×0.10 g), 2,2'-azobis(2-methylpropionitrile) (AIBN) (2×0.50 g) and methylethylketone (MEK) (3×4.0 g) were added to the reactor as initiators. Pressure was atmospheric. Temperature of the reaction mixture was raised to 230° F. Input oxygen was 20.9 mol % at a flow rate of 200 ml/min. After 24 hours, analysis by silylated gas chromatography/mass spectrometry indicated oxidation of the ortho-nitrotoluene had not initiated. Data are in Table I.

EXAMPLE II

In the procedure of Example I, ortho-nitrotoluene (9.632 g), cobalt (II) acetate (0.128 g), manganese (II) acetate (0.126 g) and sodium bromide (0.105 g), acetic acid (80.1 g) and acetic anhydride (20.0 g) were added to a glass minireactor. AIBN (2×0.50 g) and MEK (4.0 g) were added to the reactor as initiators. Temperature was 230° F. and pressure was atmospheric. After 24 hours, analysis indicated oxidation of the ortho-nitrotoluene had not been initiated. Data are in Table I.

TABLE I

| Oxidation of o-Nitrotoluene | | |
|---|---|---|
| Oxidation Number | 8887A-83 | 8887A-165 |
| o-Nitrotoluene | 19.817 g | 9.632 g |
| Co(OAc)2 | 0.257 g | 0.120 g |
| Mn(OAc)2 | 0.256 g | 0.126 g |
| NaBr | 0.210 g | 0.105 g |
| HOAc | 200.5 g | 80.1 g |
| Ac2O | — | 20.0 g |
| Co(III) | 2 × 0.10 g | — |
| AIBN | 2 × 0.50 g | 2 × 0.50 g |
| MEK | 3 × 4.0 g | 1 × 4.0 g |
| Oxidation Temperature | 230° F. | 230° F. |
| Pressure | Atmospheric | Atmospheric |
| 20.9% O2 Flow Rate | 200 ml/min | 50 ml/min |
| Hours | 24 | 24 |

The data in Table I indicate that aliphatic compounds do not act as effective co-oxidizable compounds to cause oxidation of an alkyl group ortho to a nitro group on an aromatic nucleus in the presence of a catalyst comprising cobalt (II), manganese (II), and bromine components.

The data also indicate that the presence of acetic anhydride as an oxidizable compound has no effect on oxidizing ortho-nitrotoluene at atmospheric pressure and temperature of 230° F. in the presence of the above catalyst.

EXAMPLE III

Ortho-nitrotoluene (50.043g), acetic acid (400.4g), cobalt (II) acetate (1.001g), manganese (II) acetate (1.001g), and 48% hydrobromic acid (1.367g) were charged into a one liter titanium autoclave. The oxidation was initiated by introducing air into the reactor at an initial temperature of 327° F. and an initial pressure of 250 psig. The oxidation was completed after 30 minutes and it had reached a temperature of 406° F. Ortho-nitrobenzoic acid was present in <1 mol % yield and ortho-nitrotoluene in 83 mol %. Analysis was by silylated gas chromatography/mass spectrometry. Data are in Table II.

The above yield data indicate the relative inertness of ortho-nitrotoluene to oxidation in the presence of a cobalt (II) and manganese (II) catalyst in the presence of bromine in the absence of a co-oxidizable compound at a temperature in the range of from 327° F. to about 400° F. and a pressure within the range of from 250 to 400 psig.

EXAMPLE IV

In the procedure of Example III, a run was made with a catalyst comprising cobalt, manganese, zirconium and bromine components. Acetic anhydride was added as a cooxidizable compound in Oxidation No. 11000-22. The procedure of Example I was repeated in Oxidation No. 10816-9 for comparison. Data are in Table II.

TABLE II

| Oxidation of o-Nitrotoluene | | |
|---|---|---|
| Oxidation Number | 10816-9 | 11000-22 |
| o-Nitrotoluene | 50.043 g | 50.010 g |
| Co(OAc)2 | 1.001 g | 1.008 g |
| Mn(OAc)2 | 1.001 g | 1.008 g |
| Zr(IV)[(10 Ac)2]2 | — | 0.125 g |
| HBr (48%) | 1.367 g | 1.382 g |
| HOAc | 400.4 g | 800.9 g |
| Ac2O | — | 200.1 g |
| Oxidation Temp. (°F.): | | |
| Initial–Final | 327–406 | 320–400 |
| Pressure (psig): | | |
| Initial–Final | 250–400 | 300–400 |
| Mol % in TRE | | |
| o-Nitrobenzoic Acid | <1 | 6 |
| o-Nitrotoluene | 83 | 80 |

The above yield data again indicate the relative inertness of ortho-nitrotoluene to oxidation in the presence of a catalyst comprising cobalt (II), manganese (II), zirconium (IV) and bromine.

The presence of acetic anhydride as a co-oxidizable compound acted to increase yield of ortho-nitrobenzoic acid to approximately 6 mol % at a temperature of from 320° F. to about 400° F. and a pressure of from 300 to 400 psig.

EXAMPLE V

In the procedure of Example III, an oxidation of nitromesitylene was made in the presence of a catalyst comprising cobalt (II), manganese (II) and bromine with acetic acid as solvent. The oxidation proceeded very slowly initially, with a vent oxygen reading of 20.2 vol input oxygen being 20.9 vol %. The rate of oxidation after 72 hours slowly increased over a period of 96 hours to a vent oxygen reading of 13.0 vol %. Analysis of the total reactor effluent (TRE) after 168 hours by silylated gas chromatography/mass spectrometry indicated 3,5-di-methyl-4-nitrobenzoic acid and 3,5-dimethyl-2-nitrobenzoic acid were present in a ratio of 3:1, with a yield of each of 13.4 mol % and 4.6 mol %, respectively. Unoxidized nitromesitylene was present in the total reactor effluent. 42% of the nitromesitylene was consumed. Data are in Table III.

TABLE III

| Oxidation of Nitromesitylene | |
|---|---|
| Oxidation Number | 8887A-184 |
| Nitromesitylene | 11.553 g |
| Co(OAc)$_2$ | 0.125 g |
| Mn(OAc)$_2$ | 0.125 g |
| NaBr | 0.104 g |
| HOAc | 101.6 g |
| Hours | 168 |
| Oxidation Temperature | 250° F. |
| 20.9% O$_2$ Flow Rate | 55 ml/min |
| Mole % Yield | |
| 3,5-dimethyl-4-nitrobenzoic acid | 13.4 |
| 3,5-dimethyl-2-nitrobenzoic acid | 4.6 |

The above data indicate that an aromatic alkyl group must be present for oxidation to proceed of an alkyl group ortho to a nitro group on an aromatic nucleus in the presence of a catalyst comprising cobalt (II), manganese (II) and bromine components.

EXAMPLE VI

Ortho-nitrotoluene (35 g), para-nitrotoluene (35 g), acetic acid (400 g), cobalt (II) acetate (1.0 g), manganese (II) acetate (1.0 g), and 48% hydrobromic acid (1.4 g) were charged into a one liter titanium autoclave. Ortho-nitrotoluene and para-nitrotoluene were present in equal mole ratio, the para-nitrotoluene being added to the reaction as a batch amount. The oxidation was initiated by introducing air into the reactor at an initial temperature of 293° F. and an initial pressure of 250 psig. The oxidation was completed after 70 minutes and it had reached a temperature of 360° F. at a pressure of 350 psig. Ortho-nitrobenzoic acid was found in 49.7 mol % yield and para-nitrobenzoic acid in 73.1 mol % yield (based on LC analysis of the slurry) from the oxidation. Also present in the slurry was ortho-nitrotoluene (43.9 mol %), paranitrotoluene (18.1 mol %), para-nitrobenzaldehyde (4.5 mol %), and p-nitrobenzyl acetate (3.0 mol %).

EXAMPLES VII–VIII

In the procedure of Example VI, batch oxidations of o-nitrotoluene were performed with batch additions of para-nitrotoluene. Data are in Table IV.

TABLE IV

| Batch Oxidations of o-Nitrotoluene | | |
|---|---|---|
| Example | VII | VIII |
| Oxidation Number | 8887A-195 | 10816-11 |
| o-Nitrotoluene | 25.015 g | 25.010 g |
| p-Nitrotoluene | 25.019 g | 25.003 g |
| Co(OAc)$_2$ | 1.000 g | 1.000 g |
| Mn(OAc)$_2$ | 1.001 g | 1.000 g |
| HBr (48%) | 1.264 g | — |
| NaBr | — | 0.826 g |
| HOAc | 400.3 g | 400.0 g |
| Oxidation Temp. (°F.); | | |
| Initial–Final Pressure (psig); | 300–380 | 375–422 |
| Initial–Final Mol % in TRE | 250–450 | 350–450 |
| o-Nitrobenzoic Acid | 38 | 13 |
| o-Nitrotoluene | 45 | 69 |
| o-Nitrobenzaldehyde | ND | ND |
| o-Nitrobenzyl Acetate | ND | ND |
| p-Nitrobenzoic Acid | 72 | 38 |
| p-Nitrotoluene | 19 | 47 |
| p-Nitrobenzaldehyde | 4 | 8 |
| p-Nitrobenzyl Acetate | 3 | 4 |

Example VIII indicates the loss in yield of o-nitrobenzoic acid caused by a reaction temperature greater than 360° F. in a batch procedure.

EXAMPLE IX

In a modified procedure of Example VI, ortho-nitrotoluene (35 g), para-nitrotoluene (7 g), acetic acid (300 g), cobalt (II) acetate (1 g), manganese (II) acetate (1 g), zirconium (IV) diacetate oxide (0.125 g), and 48% hydrobromic acid (1.4 g) were charged into a one liter titanium autoclave. The para-nitrotoluene and acetic acid were added in a semi-continuous procedure, with an initial charge of 7 g and 300 g, respectively. The oxidation was initiated by introducing air into the reactor at an initial temperature of 295° F. and an initial pressure of 250 psig. During the oxidation, a solution consisting of 28 g para-nitrotoluene, to give a 1:1 gram ratio and 1:1 mol ratio of o-nitrotoluene and para-nitrotoluene, and 120 g of acetic acid were added semi-continuously. LC analysis of the slurry indicated that ortho-nitrobenzoic acid was formed in 69.1 mol % yield, while p-nitrobenzoic acid was produced in 82.7 mol % yield. Ortho-nitrotoluene (24.1 mol %), p-nitrotoluene (8.1 mol %), para-nitrobenzaldehyde (1.8 mol %), and para-nitrobenzyl acetate (0.8 mol %) were also detected. Details are in Table V.

EXAMPLE X

In the procedure of Example IX, a batch oxidation of o-nitrotoluene was performed with a semi-continuous addition of 50 mole percent excess para-nitrotoluene. Data are in Table V. Yield of o-nitrobenzoic acid increased to 83 mol % as a result of the semi-continuous addition of para-nitrotoluene versus a yield of 50 mol % as in Example VI with batch addition. Details are in Table V.

TABLE V

| Semi-Continuous Co-Oxidations of o-Nitrotoluene with P—Nitrotoluene | | |
|---|---|---|
| Example Number | IX | X |
| Oxidation Number | 10816-32 | 10816-68 |
| o-Nitrotoluene | 35.008 g | 40.022 g |
| p-Nitrotoluene (Initial) | 7.001 g | 12.050 g |
| p-Nitrotoluene (Final) | 35.001 g | 60.050 g |
| Co(OAc)$_2$ | 1.001 g | 1.000 g |
| Mn(OAc)$_2$ | 1.001 g | 1.000 g |
| Zr(IV) | 0.125 g | 0.126 g |
| HBr (48%) | 1.351 g | 1.357 g |
| HOAc | 400.0 g | 400.0 g |
| Oxidation Temp. (°F.); | | |
| Initial–Final Pressure (psig); | 295–350 | 295–390 |
| Initial–Final | 250–300 | 250–300 |

TABLE V-continued

Semi-Continuous Co-Oxidations of
o-Nitrotoluene with P—Nitrotoluene

| Example Number | IX | X |
|---|---|---|
| Oxidation Number | 10816-32 | 10816-68 |
| Mol % in TRE | | |
| o-Nitrobenzoic Acid | 69 | 83 |
| o-Nitrotoluene | 24 | ND |
| o-Nitrobenzaldehyde | ND | ND |
| o-Nitrobenzyl Acetate | ND | ND |
| p-Nitrobenzoic Acid | 83 | 95 |
| p-Nitrotoluene | 8 | ND |
| p-Nitrobenzaldehyde | 2 | ND |
| p-Nitrobenzyl Acetate | 1 | ND |

ND = Not Detected

EXAMPLES XI-XII

In the procedure of Example IX, two runs were made with para-xylene.

Example XI was run at an oxidation temperature of 250° F. to 410° F. Example XII was run at an oxidation temperature of 390° F. to 420° F. Pressure in Example XI was 250–400 psig. Pressure in Example XII was 350–400 psig.

Yield of o-nitrobenzoic acid in Example XI was 96 mol %. The presence of o-nitrobenzoic acid in the product of Example XII was not detected by LC analysis, silylated gas chromatography/mass spectrometry. The yield data indicate the effect of oxidation temperature within the range of 390° F. to 420° F. at a pressure of 350 to 400 psig. The data are in Table VI.

TABLE VI

Semi-Continuous Pilot Plant.
Co-Oxidation of o-Nitrotoluene with p-Xylene

| Example | XI | XII |
|---|---|---|
| Oxidation Number | 10816-122 | 10816-165 |
| o-Nitrotoluene | 40.012 g | 40.180 g |
| p-Xylene (Initial) | 7.504 g | 7.524 g |
| p-Xylene (Final) | 107.094 g | 107.104 g |
| Co(OAc)$_2$ | 1.014 g | 1.003 g |
| Mn(OAc)$_2$ | 1.010 g | 1.004 g |
| Zr(IV) | 0.125 g | 0.124 g |
| HBr (48%) | 1.367 g | 1.356 g |
| HOAc | 400.2 g | 400.4 g |
| Oxidation-Temp. (°F.); | | |
| Initial–Final | 250–410 | 390–420 |
| Pressure (psig); | | |
| Initial–Final | 250–400 | 350–400 |
| Mol % in TRE | | |
| o-Nitrobenzoic Acid | 96 | ND |
| o-Nitrotoluene | ND | 36 |
| o-Nitrobenzaldehyde | ND | ND |
| o-Nitrobenzyl Acetate | ND | ND |
| Tetraphthalic Acid | 96 | 43 |
| p-Xylene | ND | ND |
| p-Toluic Acid | ND | ND |
| p-Tolualdehyde | ND | ND |
| 4-Carboxybenzoic Acid | <1 | 4 |

ND = Not Detected

As the data in Table VI indicate, oxidation temperature is critical for preparing ortho-nitrobenzoic acid. In Oxidation Number 10816-165, oxidation temperature was in the range of from 390° F. to 420° F. An analysis of the total reactor effluent (TRE) was unable to detect the presence of ortho-nitrobenzoic acid. In contrast, a reaction at a temperature in the range of from 250° F. to 410° F., Oxidation Number 10816-122, resulted in a reaction product containing 96 mol % yield of ortho-nitrobenzoic acid.

The data in Table VI also indicate the improved yield obtained with use of para-xylene as a co-oxidizable compound versus the yield obtained with use of para-nitrotoluene as detailed in Examples VI, IX, and X wherein ortho-nitrobenzoic acid was produced in 49.7 mol % yield, 69.1 mol % yield, and 83 mol % yield with use of para-nitrotoluene as a co-oxidizable compound.

EXAMPLE XIII

2-Nitro-p-xylene (40 g), acetic acid (400 g), cobalt (II) acetate tetrahydrate (1.0 g), manganese (II) acetate tetrahydrate (1.0 g), and 48% hydrobromic acid (1.4 g) were charged into a stirred, one liter titanium autoclave. Oxidation was initiated at an initial temperature of 356° F. under a 300 psig nitrogen atmosphere by introducing 20.9 vol % O$_2$ in nitrogen into the reactor at a rate of 18 ft$^3$/hr. Oxidation temperature was controlled between 356°–451° F. and the pressure was gradually increased to 500 psig. The reaction was terminated when the vent O$_2$ (monitored via a Beckman Model 715 Process Oxygen Monitor) had reached a steady 19 vol %. 2-Nitroterephthalic acid was found in a 2 mol % yield while 20% of the 2-nitro-p-xylene had not reacted.

Example XIII indicates that 2-nitro-p-xylene cannot be successfuly oxidized with molecular oxygen using heavy metal catalysts and a bromine component where no co-oxidizable compound is present.

EXAMPLE XIV

2-Nitro-p-xylene (40 g), acetic acid (300 g), cobalt (II) acetate tetrahydrate (1.0 g), manganese (II) acetate tetrahydrate (1.0 g), zirconium (IV) diacetate oxide (0.13 g), and 48% hydrobromic acid (1.4 g) were charged into a stirred, one liter titanium autoclave. Oxidation was initiated at an initial temperature of 325° F. under a 250 psig nitrogen atmosphere by introducing 20.9 volume % O$_2$ in nitrogen into the reactor at a rate of 18 ft$^3$/hr. After the initial oxygen uptake had ceased, a solution consisting of toluene in acetic acid (0.5 g toluene per ml of solution) was added to the reactor semi-continuously via a single-headed Milton Roy pump at a flow rate of 2–2.5 ml/minute. Oxidation temperature was maintained at an average of 370° F. during the semi-continuous addition of toluene (0.65 moles), followed by a rapid temperature ramp to 405° F. and a pressure of 300 psig. Oxidation was terminated when the vent O$_2$ (monitored via a Beckman Model 715 Process Oxygen Monitor) had reached a steady 19 volume %. 2-Nitroterephthalic acid was found in a 68 mol % yield and benzoic acid was found in a 94 mol % yield from the oxidation. Also present was 0.6 mol % 2-nitro-p-xylene.

Example XIV shows that 2-nitro-p-xylene is successfully oxidized in 68% yield to 2-nitroterephthalic acid when toluene is included as a co-oxidizable compound in the reaction mixture. In this example the toluene was added semi-continuously to the oxidation reaction. In addition, toluene, the co-oxidizable material was oxidized in 96% yield to benzoic acid.

EXAMPLE XV

2-Nitro-p-xylene (40 g), acetic acid (300 g), cobalt (II) acetate tetrahydrate (1.0 g), manganese (II) acetate tetrahydrate (1.0 g), zirconium (IV) diacetate oxide (0.13 g), and 48% hydrobromic acid (1.4 g) were charged into a stirred, one liter titanium autoclave. Oxidation was initiated at an initial temperature of 325° F. under a 250 psig nitrogen atmosphere by introducing 20.9 volume % oxygen into the reactor at a flow rate of 18 ft³/hr. After the initial oxygen uptake had ceased, a solution consisting of toluene in acetic acid (0.7 g toluene per ml of solution) was added semi-continuously to the reactor via a single-headed Milton Roy pump at a flow rate of 2–2.5 ml/minute. Oxidation temperature was maintained at an average of 383° F. during the semi-continuous addition of toluene (0.87 moles), followed by a rapid temperature ramp to 415° F. and a pressure of 350 psig. Oxidation was terminated when the vent $O_2$ had reached a steady 19 volume %. Analysis of the reaction products indicated that 2-nitroterephthalic acid was formed in a 74 mole % yield, while benzoic acid was formed in a 91 mole % yield. Toluene and 2-nitro-p-xylene were not detected.

Example XV indicates that the yield of 2-nitroterephthalic acid can be improved by increasing the oxidation reaction temperature and pressure and by increasing the amount of toluene, the co-oxidizable compound. In this example, the yield of 2-nitroterephthalic acid was increased to 74 mole % compared to the 68 mole % yield of Example XIV.

We claim:

1. A process for producing an ortho-nitroaromatic acid by oxidizing an ortho-nitroaromatic having at least one nitro group ortho to at least one oxidizable group which process comprises oxidizing said ortho-nitroaromatic with molecular oxygen in a reaction zone at a temperature within the range of from about 250° F. to about 400° F. and a pressure from about 150 psig to about 400 psig in the presence of an inert reaction medium, while maintaining a liquid phase in said zone, in the conjoint presence of a co-oxidizable compound and a heavy metal catalyst and bromine, and subsequent to the oxidation of said ortho-nitroaromatic to an ortho-nitroaromatic acid elevating the temperature to a temperature within the range of from about 250° F. to about 430° F. to oxidize the remaining co-oxidizable compound, and recovering the ortho-nitroaromatic acid.

2. A process as defined in claim 1 wherein the heavy metal has an atomic number of 23 to 28 inclusive.

3. A process as defined in claim 1 wherein bromine is in ionic form.

4. A process as defined in claim 1 wherein said co-oxidizable compound is an alkyl aromatic compound.

5. A process as defined in claim 4 wherein said alkyl aromatic compound is selected from the group consisting of para-xylene, para-nitrotoluene, meta-xylene and toluene.

6. A process as defined in claim 1 wherein the cooxidizable compound is para-xylene.

7. A process as defined in claim 1 wherein the cooxidizable compound is toluene.

8. A process as defined in claim 1 wherein the heavy metal is manganese.

9. A process as defined in claim 1 wherein the heavy metal is cobalt.

10. A process as defined in claim 1 wherein the heavy metal comprises manganese and cobalt.

11. A process as defined in claim 1 wherein the heavy metal comprises manganese, cobalt and zirconium.

12. A process as defined in claim 1 carried out in the presence of a monocarboxylic acid having about 1 to about 8 carbon atoms in the molecule.

13. The process of claim 12 wherein the monocarboxylic acid is acetic acid.

14. The process of claim 1 wherein the co-oxidizable compound is added semi-continuously.

15. A process for producing an ortho-nitroaromatic acid by oxidizing an ortho-nitroaromatic having at least one nitro group ortho to at least one methyl group which process comprises oxidizing said ortho-nitroaromatic with molecular oxygen in a reaction zone at a temperature within the range from about 250° F. to about 400° F. and a pressure from about 150 psig to about 400 psig in the presence of an inert reaction medium, while maintaining a liquid phase in said zone, in the conjoint presence of a co-oxidizable compound and a heavy metal catalyst and bromine, and subsequent to the oxidation of said ortho-nitroaromatic to an ortho-nitroaromatic acid elevating the temperature to a temperature within the range of from about 250° F. to about 430° F. to oxidize the remaining co-oxidizable compound, and recovering the ortho-nitroaromatic acid.

16. A process as defined in claim 15 wherein the heavy metal has an atomic number of 23 to 28 inclusive.

17. A process as defined in claim 15 wherein bromine is in ionic form.

18. A process as defined in claim 15 wherein said co-oxidizable compound is an alkyl aromatic compound.

19. A process as defined in claim 18 wherein said alkyl aromatic compound is selected from the group consisting of para-xylene, para-nitrotoluene, meta-xylene, and toluene.

20. A process as defined in claim 19 wherein the co-oxidizable compound is para-xylene.

21. A process as defined in claim 19 wherein the co-oxidizable compound is toluene.

22. A process as defined in claim 15 wherein the heavy metal is manganese.

23. A process as defined in claim 15 wherein the heavy metal is cobalt.

24. A process as defined in claim 15 wherein the heavy metal comprises manganese and cobalt.

25. A process as defined in claim 15 wherein the heavy metal comprises manganese, cobalt and zirconium.

26. A process as defined in claim 15 wherein the co-oxidizable compound is added semi-continuously during the oxidation.

27. A process as defined in claim 15 carried out in the presence of a monocarboxylic acid having about 1 to about 8 carbon atoms in the molecule.

28. The process of claim 27 wherein the monocarboxylic acid is acetic acid.

29. The process of claim 15 wherein said ortho-nitroaromatic is ortho-nitrotoluene and said ortho-nitroaromatic acid is ortho-nitrobenzoic acid.

30. The process of claim 29 wherein the oxidation of ortho-nitrotoluene is carried out at a temperature of from about 250° F. to about 360° F.

31. The process of claim 29 wherein the oxidation of ortho-nitrotoluene is carried out at a temperature of from about 295° F. to about 350° F.

32. The process of claim 29 wherein the oxidation of the remaining co-oxidizable compound is carried out at a temperature of from about 295° F. to about 410° F.

33. The process of claim 29 wherein the oxidation of the remaining co-oxidizable compound is carried out at a temperature of from about 380° F. to about 410° F.

34. The process of claim 29 wherein said co-oxidizable compound is para-xylene.

35. The process of claim 29 wherein said co-oxidizable compound is para-nitrotoluene.

36. The process of claim 29 wherein said heavy metal comprises manganese and cobalt.

37. The process of claim 29 wherein said heavy metal comprises manganese, cobalt and zirconium.

38. The process of claim 29 wherein the co-oxidizable compound is added semi-continuously.

39. The process of claim 29 carried out in the presence of a monocarboxylic acid having about 1 to about 8 carbon atoms in the molecule.

40. The process of claim 39 wherein the monocarboxylic acid is acetic acid.

41. The process of claim 29 wherein ortho-nitrobenzoic acid is recovered by cooling the total reactor effluent to a temperature of about 220° F. to about 260° F., removing the co-oxidizable compound product acid by filtration, stripping the mother liquor, extracting the mother liquor with water at a temperature of about 180° F. to about 212° F., cooling the mother liquor from about 35° F. to about 65° F. and filtering the mother liquor to give ortho-nitrobenzoic acid.

42. The process of claim 15 wherein said ortho-nitroaromatic is 2-nitro-paraxylene and said ortho-nitroaromatic acid is 2-nitroterephthalic acid.

43. The process of claim 42 wherein the oxidation of 2-nitro-paraxylene is carried out at a temperature of from about 250° F. to about 400° F.

44. The process of claim 42 wherein the oxidation of 2-nitro-paraxylene is carried out a temperature of from about 295° F. to about 400° F.

45. The process of claim 42 wherein the oxidation of the remaining co-oxidizable compound is carried out at a temperature of from about 380° F. to about 430° F.

46. The process of claim 42 wherein the oxidation of the remaining co-oxidizable compound is carried out at a temperature of from about 350° F. to about 420° F.

47. The process of claim 42 wherein said co-oxidizable compound is toluene.

48. The process of claim 42 wherein said inert reaction medium is benzoic acid.

49. The process of claim 42 wherein said heavy metal comprises manganese and cobalt.

50. The process of claim 42 wherein said heavy metal comprises manganese, cobalt and zirconium.

51. The process of claim 42 wherein the co-oxidizable compound is added semi-continuously.

52. The process of claim 42 carried out in the presence of a monocarboxylic acid having about 1 to about 8 carbon atoms in the molecule.

53. The process of claim 52 wherein the monocarboxylic acid is acetic acid.

54. A process for producing ortho-nitrobenzoic acid, which process comprises reacting ortho-nitrotoluene with molecular oxygen in a reaction zone, containing an aliphatic monocarboxylic acid containing about 2 to about 4 carbon atoms, while maintaining a liquid phase in said zone, wherein para-nitrotoluene is added throughout the reaction and wherein the reaction is carried out in the presence of cobalt and manganese and bromine, said reacting being carried out at a temperature within the range of from about 250° F. to about 360° F. and a pressure of from about 150 psig to about 400 psig, after the ortho-nitrotoluene has been oxidized to ortho-nitrobenzoic acid, elevating the temperature to a temperature within the range of from about 380° F. to about 410° F. in order to oxidize the remaining co-oxidizable compound, and recovering the ortho-nitrobenzoic acid.

55. The process of claim 54 wherein the monocarboxylic acid is acetic acid.

56. The process of claim 54 wherein the oxidation of said ortho-nitrotoluene is carried out at a temperature of about 250° F. to about 350° F.

57. The process of claim 55 wherein the oxidation of said ortho-nitrotoluene is carried out at a temperature of about 295° F. to about 350° F.

58. The process of claim 55 wherein ortho-nitrobenzoic acid is recovered by cooling the total reactor effluent to a temperature of about 220° F. to about 260° F., stripping the mother liquor, extracting the mother liquor with water at a temperature of about 180° F. to about 212° F., cooling the mother liquor to about 35° F. to about 65° F. and filtering the mother liquor to give ortho-nitrobenzoic acid.

* * * * *

UNITED STATES PATENT AND TRADEMARK OFFICE
CERTIFICATE OF CORRECTION

PATENT NO. : 4,906,771

DATED : March 6, 1990

INVENTOR(S) : David A. Young and Mary E. Volling

It is certified that error appears in the above-identified patent and that said Letters Patent is hereby corrected as shown below:

Column 7, line 41, "orthonitrobenzoic" should be --ortho-nitrobenzoic--

Column 8, line 21, "orthonitroaromatics" should be --ortho-nitroaromatics--

Column 10, line 29, "cooxidizable" should be --co-oxidizable--

Column 10, line 67, "vol input" should be --vol %, input--

Column 11, line 49, "paranitrotoluene" should be --para-nitrotoluene--

Column 11, line 67, "400.3 g
                     400.0 g" should be --400.3 g 400.0 g--

Column 15, lines 50-51, "cooxidizable" should be --co-oxidizable--

Column 15, 52-53, "cooxidizable" should be --co-oxidizable--

Signed and Sealed this

Ninth Day of July, 1991

*Attest:*

HARRY F. MANBECK, JR.

*Attesting Officer*    *Commissioner of Patents and Trademarks*